(12) United States Patent
Xuan et al.

(10) Patent No.: US 9,330,333 B2
(45) Date of Patent: May 3, 2016

(54) METHOD AND APPARATUS FOR IMAGE CONTENT-BASED AUTOMATIC BRIGHTNESS DETECTION

(75) Inventors: Xiao Xuan, Beijing (CN); Romain Areste, Waukesha, WI (US); Vivek Walimbe, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 98 days.

(21) Appl. No.: 14/007,976

(22) PCT Filed: Mar. 30, 2011

(86) PCT No.: PCT/CN2011/000541
§ 371 (c)(1),
(2), (4) Date: Sep. 27, 2013

(87) PCT Pub. No.: WO2012/129724
PCT Pub. Date: Oct. 4, 2012

(65) Prior Publication Data
US 2014/0016868 A1    Jan. 16, 2014

(51) Int. Cl.
*G06K 9/00* (2006.01)
*G06K 9/46* (2006.01)
*A61B 6/00* (2006.01)
*G06T 7/00* (2006.01)

(52) U.S. Cl.
CPC ............ *G06K 9/4661* (2013.01); *A61B 6/4233* (2013.01); *A61B 6/465* (2013.01); *A61B 6/469* (2013.01); *A61B 6/52* (2013.01); *A61B 6/542* (2013.01); *A61B 6/545* (2013.01); *G06T 7/0081* (2013.01); *G06T 2207/10121* (2013.01); *G06T 2207/20021* (2013.01); *G06T 2210/41* (2013.01)

(58) Field of Classification Search
None
See application file for complete search history.

(56) References Cited

U.S. PATENT DOCUMENTS

| 5,574,764 | A | 11/1996 | Granfors et al. |
| 6,795,526 | B2 | 9/2004 | Kump et al. |

(Continued)

FOREIGN PATENT DOCUMENTS

| CN | 1812481 A | 8/2006 |
| CN | 1991971 A | 7/2007 |

(Continued)

OTHER PUBLICATIONS

International Search Report, ISA China, dated Dec. 22, 2011.

(Continued)

*Primary Examiner* — Hadi Akhavannik
(74) *Attorney, Agent, or Firm* — GE Global Patent Operation; Marc A. Vivenzio (57) ABSTRACT

A method and apparatus for image automatic brightness detection. The method includes determining region of interest (ROI) candidates in an image, extracting features from each of the ROI candidates, selecting the optimum ROI based on weighted score of each of the ROI candidate, and calculating brightness value of the selected optimum ROI candidate as brightness feedback. The method and apparatus for image automatic brightness detection according to embodiments of the present invention, can automatically detect the point of interest for clinicians, and then provide a more accurate feedback to the imaging system, in order to provide a more efficient dose management in the imaging system and thus to achieve constant image quality without wasting any dose, thereby further optimizing the dose/IQ performance and the high efficient utilization of the system.

14 Claims, 4 Drawing Sheets

(56) References Cited

U.S. PATENT DOCUMENTS

| | | |
|---|---|---|
| 7,630,020 B2 | 12/2009 | Fukuda |
| 7,724,983 B2 | 5/2010 | Lee |
| 8,798,352 B2 | 8/2014 | Miyamoto |
| 2004/0095477 A1 | 5/2004 | Maki et al. |
| 2007/0248268 A1* | 10/2007 | Wood .......................... 382/195 |
| 2008/0253660 A1 | 10/2008 | Matsushita |
| 2009/0279663 A1 | 11/2009 | Miyamoto |
| 2010/0025384 A1 | 2/2010 | Todorow |
| 2010/0253846 A1 | 10/2010 | Fergason et al. |

FOREIGN PATENT DOCUMENTS

| | | |
|---|---|---|
| CN | 101105862 A | 1/2008 |
| CN | 101945275 A | 1/2011 |
| JP | 56137178 A | 10/1981 |
| JP | 08078186 A | 3/1996 |
| JP | 09106016 A | 4/1997 |
| JP | 2003284708 A | 10/2003 |
| JP | 2009268699 A | 11/2009 |
| JP | 2010004543 A | 1/2010 |
| JP | 2012235948 A | 12/2012 |

OTHER PUBLICATIONS

Unofficial English translation of JPO Office Action issued in connection with corresponding JP Application No. 2014-501386 on Jan. 6, 2015.

Unofficial English translation of Chinese Office Action issued in connection with corresponding CN Application No. 201180069946.8 on May 29, 2015.

Unofficial translation of Japanese Office Action from corresponding JP Application No. 2014-501386 dated Jul. 21, 2015.

Unofficial English Translation of Japanese Office Action issued in connection with corresponding JP Application No. 2014501386 on Feb. 16, 2016.

* cited by examiner

METHOD AND APPARATUS FOR IMAGE CONTENT-BASED AUTOMATIC BRIGHTNESS DETECTION

CROSS-REFERENCE TO RELATED APPLICATIONS

This is a National Stage Application under 35 U.S.C. §371 of prior-filed, co-pending International Application No. PCT/CN2011/000541, filed on Mar. 30 2011, which is hereby incorporated by reference in its entirety.

TECHNICAL FIELD

The present invention relates to imaging technology, and more particularly, to a method and apparatus for image automatic brightness detection.

BACKGROUND OF THE INVENTION

Automatic Brightness Detection (ABD) is essential to an imaging detection, particularly to a real-time X-ray fluoroscopy. Automatic brightness detection comprises detecting the brightness of a given frame in a small region of interest (ROI), which is used to provide feedback to a system for automatic adjustment of imaging technical parameters (e.g., kV, mA . . . ). Existing methods for automatic brightness detection mainly rely on manual selection of a fixed ROI or simply move the ROI to a low grey-scale (thick anatomy) region. Such methods may give too low or too high signal in clinic practice, since the region of interest does not always remain constant in the view of a clinician, and is not always in the thickest anatomy.

Therefore, there is a need for method and apparatus for automatic brightness detection that can automatically detect a point of interest for a clinician, and then provide a more accurate feedback to an imaging system.

SUMMARY OF THE INVENTION

An object of the present invention is to overcome disadvantages in the prior art by providing a method for image content-based ROI detection that provides a better representation of a point of interest for a clinician in an actual imaging scene by detecting and tracking contrast agent in an image. To achieve this object, the present invention will take the following technical solutions.

According to an embodiment of the present invention, there is provided a method for image automatic brightness detection, the method comprising steps of: determining ROI candidates in an image; extracting features from each of the ROI candidates; selecting the optimum ROI candidate based on weighted score of each of the ROI candidates; and calculating brightness value of the selected optimum ROI candidate as brightness feedback.

According to an embodiment of the present invention, said determining ROI candidates in an image comprises calculating sizes of the ROI candidates and their overlapping in each of directions.

According to an embodiment of the present invention, said extracting features from each of the ROI candidates comprises extracting the features that are based on statistic characteristics of a grey-scale value for a pixel, the features that are based on relation between pixels, and/or the features that are based on image transformation. According to an embodiment of the present invention, the features extracted include negative mean of pixels with maximum, negative mean of pixels with minimum, and edge information extracted by applying edge detection filter.

According to an embodiment of the present invention, the pixels with the maximum refer to upper pixels from a predefined percentage of all pixel values ranked in descending order, and the pixels with the minimum refer to upper pixels from a predefined percentage of all pixel values ranked in ascending order.

According to an embodiment of the present invention, the step of selecting the optimum ROI candidate based on weighted score of each of the ROI candidates further comprises steps of: queuing all of the ROI candidates in descending order for each of the features, and determining serial number of each of the ROI candidates in the queue as a score of the feature of the ROI candidate; and calculating the weighted score of each of the ROI candidates by multiplying the scores of the extracted features of each of the ROI candidates respectively by the predetermined weighting coefficient of the feature to obtain respective products and summing the products; wherein the ROI candidate with the smallest weighted score is selected as the optimum ROI.

Wherein the predetermined weighting coefficient is obtained by means of training for each of the extracted features.

According to an embodiment, calculating the brightness value of the selected optimum ROI candidate comprises calculating mean values or median values of pixels; the pixels used to calculate the brightness value may include all pixels, the pre-selected sampled pixels in the ROI, or a predetermined percentage of pixel intensity.

According to an embodiment of the present invention, there is provided an apparatus for image automatic brightness detection, comprising: a determining module for determining ROI candidates in an image; an extracting module for extracting features from each of the ROI candidates; a selecting module for selecting the optimum ROI candidate based on weighted score of each of the ROI candidates; and a feedback module for calculating brightness value of the selected optimum ROI candidate as brightness feedback.

According to an embodiment of the present invention, the determination of the ROI candidates by the determining module comprises calculating sizes of the ROI candidates and their overlapping in each of directions.

According to an embodiment of the present invention, the extracting module extracts the features that are based on statistic characteristics of a grey-scale value for a pixel, the features that are based on relation between pixels, and/or the features that are based on image transformation. According to an embodiment of the present invention, the features extracted by the extracting module include negative mean of pixels with maximum, negative mean of pixels with minimum, and edge information extracted by applying edge detection filter.

In an embodiment of the present invention, the pixels with the maximum refer to upper pixels from a predefined percentage of all pixel values ranked in descending order, and the pixels with the minimum refer to upper pixels from a predefined percentage of all pixel values ranked in ascending order.

According to an embodiment of the present invention, the selecting module further comprises: a queuing module for queuing all of the ROI candidates in descending order for each of the features, and determining serial number of each of the ROI candidates in the queue as a score of the feature of the ROI candidate; and a calculating module for calculating the weighted score of each of the ROI candidates by multiplying the scores of the extracted features of each of the ROI candidates respectively by the predetermined weighting coefficient of the feature to obtain respective products and summing the products; wherein the ROI candidate with the smallest weighted score is selected as the optimum ROI.

According to an embodiment of the present invention, the predetermined weighting coefficient is obtained by means of training for each of the extracted features.

According to an embodiment of the present invention, the calculation of the brightness value of the selected optimum ROI candidate by the feedback module comprises calculating mean values or median values of pixels; the pixels used to calculate the brightness value may include all pixels, the pre-selected sampled pixels in the ROI, or a predetermined percentage of pixel intensity.

According to an embodiment of the present invention, there is provided an imaging system, comprising a ROI pre-defining module, a predefined ROI adjusting module, an image automatic brightness detection apparatus, a ROI display selecting module, and a ROI real-time adjusting module. The ROI predefining module is connected to the predefined ROI adjusting module to input the predefined ROI to the predefined ROI adjusting module; and the predefined ROI adjusting module is connected to the image automatic brightness detection apparatus, which uses the predefined or adjusted predefined ROI as initial position. The image automatic brightness detection apparatus is also connected with the ROI display selecting module to input the current ROI into the ROI display selecting module for display; and the image automatic brightness detection apparatus is connected with the ROI real-time adjusting module to set its ROI based on the adjusted ROI from the ROI real-time adjusting module.

According to an embodiment of the present invention, when the imaging system is operating, the ROI predefining module may be turned on or off, for making a determination whether or not the predefined ROI is inputted by a user. According to an embodiment of the present invention, when the imaging system is operating, the predefined ROI adjusting module may be turned on or off, for making a determination whether or not the predefined ROI is adjusted. According to an embodiment of the present invention, when the imaging system is operating, the ROI display selecting module may be turned on or off, for making a determination whether or not ROI position is reviewed in real-time. According to an embodiment of the present invention, when the imaging system is operating, the ROI real-time adjusting module may be turned on or off, for making a determination whether or not the ROI position is manually adjusted in real-time.

According to an embodiment of the present invention, the image automatic brightness detection apparatus included in the imaging system is the image automatic brightness detection apparatus according to the second aspect of the embodiment of the present invention.

The method and apparatus for image automatic brightness detection as well as the imaging system according to embodiments of the present invention can automatically detect a point of interest for a clinician, and then provide a more accurate feedback to the imaging system. With the use of such method and apparatus for automatic brightness detection, the dose management in a fluoroscopic system will become more efficient, which means that a constant image quality may be obtained without wasting any dose. The feedback strength may be configured for every specific application, acquisition setting, etc., thereby further optimizing the dose/IQ performance and the high efficient utilization of the system.

The present invention will be specifically described below by way of embodiments in connection with the accompanying drawings, throughout which the same or substantially same components are indicated by the same reference numbers.

DETAILED DESCRIPTION OF THE INVENTION

Figure 1:
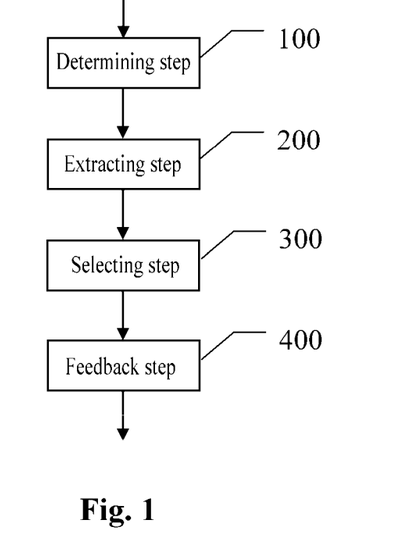
FIG. 1 is a schematic flow diagram of a method for image automatic brightness detection according to an embodiment of the present invention.

The method for image analysis according to an embodiment of the present invention comprises, for example, a series of steps for an X-ray fluoroscopic sequence that are dynamically performed. The calculation relates to, for example, each of frames or a down-sampled subset of frames in the X-ray fluoroscopic sequence. As shown in FIG. 1, a method for image automatic brightness detection according to an embodiment mainly comprises a determining step 100, an extracting step 200, a selecting step 300 and a feedback step 400. The determining step 100 is used to determine ROI candidates in an image; and the extracting step 200 is used to extract features from each of the ROI candidates; and in the selecting step 300, the optimum ROI candidate is selected based on weighted score of each of the ROI candidates; and in the feedback step 400, the brightness value of the selected optimum ROI candidate is calculated as brightness feedback. These steps will be specifically described below.

Figure 2:
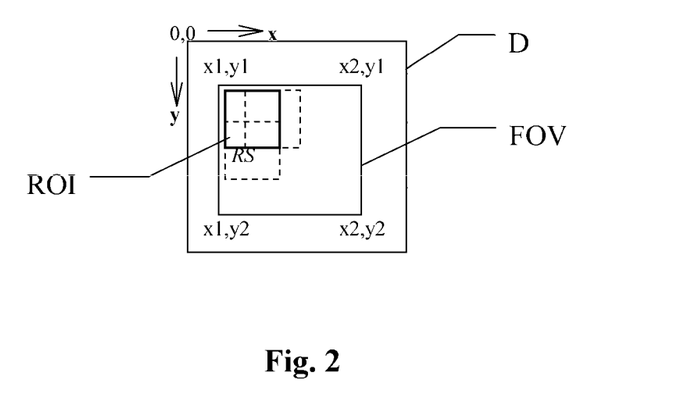
FIG. 2 is a schematic diagram of determining a region of interest (ROI) candidate according to an embodiment of the present invention.

The ROI candidates are first determined and, according to an embodiment, some ROI candidates may be selected with the same size and shape (Step 100). It is assumed that the position of the object being illuminated is not limited, and then the selection of the ROI candidates should cover the entire field of view, such as the entire field of view of X ray, as possible. Depending on the actual need, the ROI may be any shape, such as a rectangle, circle, and square etc. . . . In actual systems, the field of view may also be a rectangle, circle, or polygon, etc. As shown in FIG. 2, when the field of view FOV in the detected region D is a rectangle and ROI is a square, the ROI candidate may be determined by the following manner. The ROI candidates are overlapped squares, uniformly covering the region in the field of view (FOV). The vertex for the field of view may be obtained from the system feedback. Typically, using a rectangular field of view, it may be assumed that the vertex coordinates of the field of view are: (x1, y1), (x2, y1), (x2, y2), (x1, y2), as shown in FIG. 2, and thus the size RS of the ROI candidate is:

$$RS=\min(256,\min(x2-x1,y2-y1));$$

The overlapping is calculated in each of directions, considering that the field of view is not always a square, then:

Overlap $X=\min(RS/2,(Nx*RS-(x2-x1))/(Nx-1))$;

Overlap $Y=\min(RS/2,(Ny*RS-(y2-y1))/(Ny-1))$;

where Nx and Ny are the maximum numbers of the ROI candidates in each of directions, and Nx*Ny is the maximum total number of the ROI candidates. According to the time requirement of the algorithm, the sizes of Nx and Ny are adjustable.

When the ROI is a rectangle, circle, ellipse and other shapes, similar methods may also be used to select the ROI candidates simply by means of calculation with setting RS in X direction and Y direction to different parameters. The length of RS in X direction represents the side length of the minimal circumscribed rectangle of the ROI in X direction, and the length of RS in Y direction represents the side length of the minimal circumscribed rectangle of the ROI in Y direction. When the fields of view are different shapes, similar methods may also be used to select the ROI candidates, provided that the moving range of the ROI is limited within the field of view.

An image may include four kinds of regions, raw radiation, anatomy, contrast agent, and foreign object. For automatic brightness detection (ABD) algorithm, if the contrast agent is used, the ROI covering the contrast area should be selected; and if no contrast agent is used, the ROI covering the anatomy should be selected. However, in any cases, the ROI with the raw radiation or the foreign object should be discarded.

In order to detect the kind of region covered by each of the ROI candidates, it is required to extract several features from each of the ROIs (Step 200), these features include, but are not limited to, the features that are based on the statistic characteristics of a grey-scale value for a pixel, such as mean value, median value, etc.; the features that are based on the relation between pixels, such as one obtained by using the edge operator to filter the image and extracting the mean value of the filtered pixels as the feature; the features that are based on the image transformation, such as one obtained by applying a wavelet transformation and extracting the mean value of the transformed pixels as the feature. Considering such factors as time complexity etc., in an embodiment, it is preferable to use the following three kinds of relative effective features:

Tmax: negative mean of the maximum 10% pixels;
Tmin: negative mean of the minimum 10% pixels;
Edge: edge information extracted by applying the edge detection filter.

These features are designed based on fluoroscopic image contents, for example, the raw radiation has a relative low Tmax value, and then the contrast area usually has a high Tmin value and Edge value. The goal of selecting the features is to distinguish the ROI with the contrast agent and without the raw radiation. To prepare for the next step, it is assumed that the larger the value of the feature is, the closer the ROI is to the target. Therefore, if necessary, a negative sign should be added before the value of the feature, such as Tmax, and it is defined as the negative mean of the minimum 10% pixels. Since the ROI with the contrast agent has usually a relative small mean of pixels, the negative mean is larger.

Figure 3:
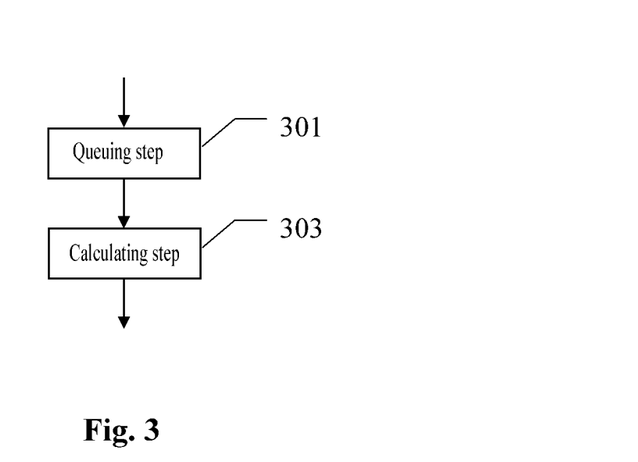
FIG. 3 is a schematic flow diagram of selecting the optimum region of interest (ROI) candidate according to an embodiment of the present invention.

As mentioned above, the selected ROI will cover the contrast area or anatomy, but avoid the raw radiation and foreign object. In an embodiment of the present invention, based on these extracted features, the optimum ROI is selected by means of the method for weighted score (Step 300). This method does not need any threshold, but only relies on the natural brightness relations among different regions, and therefore it is robust for the varying imaging technologies. As shown in FIG. 3, according to an embodiment, based on the weighted score of each of the ROI candidates, selecting the optimum ROI candidate further comprises a queuing step 301 and a calculating step 303. Detailed description is as follows.

Firstly, for each of the features, all of the ROI candidates are queued in descending order (Step 310), and the serial number of each of the ROI candidates in the queue is determined as the score of the feature of the ROI candidate. For example, there are three ROI candidates, i.e., ROI1, ROI2 and ROI3, if values of their Tmax are respectively 170, 210 and 150, the queue of ROIs for the feature Tmax is ROI1(2), ROI2(1) and ROI3(3), and then the scores of ROI1, ROI2 and ROI3 are respectively 2, 1 and 3. As mentioned above, the larger the value of the feature is, the more optimal the ROI is, and therefore, the optimum ROI should have a relative small score after the queuing.

Secondly, the weighted score of each of the ROIs is calculated (Step 320) O

Weighted Score=$[w1,w2,w3]*[S1,S2,S3]^T$;

a weighting coefficient (represented by wi) is set for the feature i (i=1-3), this is because each of the features is not equally completed when different regions are differentiated. After the feature is selected, the weight value, i.e., the weighting coefficient, may be obtained by means of training. In an embodiment, if the features Tmax, Tmin and Edge are selected, the weight values obtained by means of the training are respectively [1, 1, 1.5], and applying the weight values on the experimental data set may achieve a better effect. Therefore, during the calculation, the weighting coefficients of Tmax, Tmin and Edge may be respectively set to [1, 1, 1.5]. Si represents the score of the ROI for feature i.

Finally, the ROI with the smallest weighted score is selected as the optimum ROI. The above-mentioned queuing and calculating processes and the calculation results according to an embodiment are shown in Table 1 below.

TABLE 1

Table for Weighted Score Calculation

| | Queue | | | Weighted Score |
|---|---|---|---|---|
| | S1 | S2 | S3 | 1*S1 + 1*S2 + 1.5*S3 |
| ROI 1 | 1 | 2 | 1 | 4.5 (the optimum ROI) |
| ROI 2 | 2 | 1 | 3 | 7.5 |
| ROI 3 | 3 | 3 | 2 | 9 |

The weighting solution may also be varied based on the application to be performed, in order to illustrate different clinic point of interest for a radiologist.

After the above-mentioned steps, at least one ROI covering the point of interest for a clinician is selected. Next, the brightness value of the selected ROI is calculated in order to represent the signal level of the point of interest, and is used as the brightness feedback (Step 400). As an example, the average pixel value of the ROI may be used as the brightness feedback. Such an example includes, but is not limited to, the mean value, median value, etc., of pixels. The pixels selected to be used for calculating the metric may include all of pixels, the pre-selected sampled pixels in the ROI, a predetermined percentage of the pixel intensity, etc.

The method according to embodiments of the present invention can automatically detect the point of interest for a clinician, and then provide a more accurate feedback to the fluoroscopic system. With the use of this ABD method, the dose management in a fluoroscopic system will become more efficient, which means that a constant image quality can be obtained without wasting any dose. The feedback strength may be configured for every specific application, acquisition setting, etc., thereby further optimizing the dose/IQ performance and the high efficient utilization of the system.

Compared to existing ABD methods, the image content-based ABD method according to embodiments of the present invention can dynamically and automatically adjust the size and number of ROI based on the field of view region, whereas existing methods typically use the fixed size and number of ROI; and the image content-based ABD method according to embodiments of the present invention can extract and analyze a series of image-based features, whereas existing methods have no feature analysis of the ROI and the only information used by them is mean value of grey-scale values; and the image content-based ABD method according to embodiments of the present invention selects the optimum ROI based on the weighted score without any system feedback and is robust for the varying imaging technologies, whereas previous ABD methods do not involve this part. In addition, the method according to embodiments of the present invention can avoid the effect of the raw radiation, and if there is the contrast agent, it can also track the contrast area, whereas previous ABD methods cannot do so.

Figure 4:
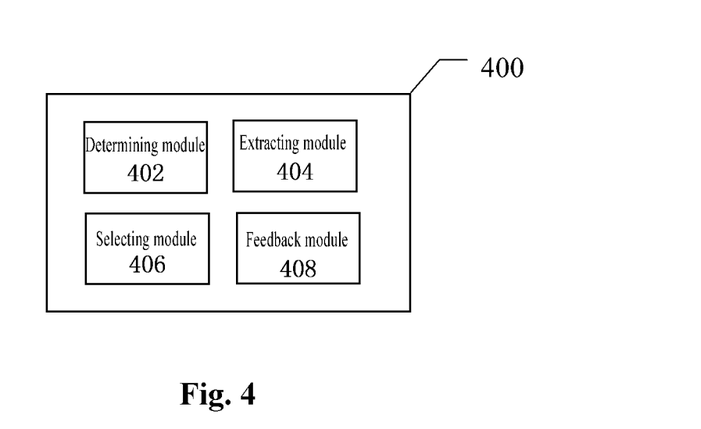
FIG. 4 is a schematic diagram of an apparatus for image automatic brightness detection according to an embodiment of the present invention.

FIG. 4 is a schematic diagram of an image automatic brightness detection apparatus 400 according to an embodiment of the present invention. The apparatus 400 mainly comprises a determining module 402, an extracting module 404, a selecting module 406 and a feedback module 408. These modules may be implemented by means of software, hardware, firmware, or any combination thereof, wherein:
the determining module 402 is used to perform step 100;
the extracting module 404 is used to perform step 200;
the selecting module 406 is used to perform step 300; and
the feedback module 408 is used to perform step 400.

Figure 5:
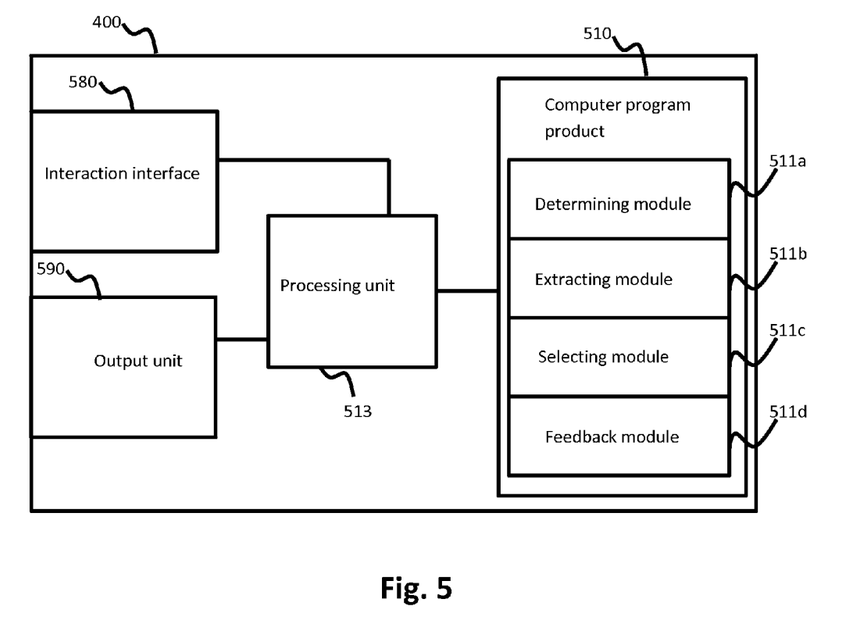
FIG. 5 is a schematic diagram of an apparatus for image automatic brightness detection according to an embodiment of the present invention.

FIG. 5 is an embodiment of another image automatic brightness detection apparatus 400. The apparatus 400 comprises a processing unit 513, such as MCU, DSP or CPU, etc. The processing unit 513 may be a single unit or multiple units to perform different steps described. In addition, the apparatus 400 may optionally include an interaction interface 580 and an output unit 590 for inputting image data and outputting feedback information. Furthermore, the apparatus 400 may also include at least one computer program product 510 in the form of non-volatile memory, such as EEPROM, flash, or hard disk drive, etc. The computer program product 510 comprises computer program 511 comprising program codes which, when executed, causes the apparatus 400 to perform the steps as shown in FIG. 1.

In particular, program codes contained in the computer program 511 in the apparatus 400 include: determining module 511a for performing step 100; an extracting module 511b for performing step 200; a selecting module 511c for performing step 300; a feedback module 511d for performing step 400. In other words, when different modules 511a-511d are executed on the processing unit 513, they correspond respectively to the modules 402, 404, 406 and 408 as shown in FIG. 4.

The image automatic brightness detection apparatus 400 according to the embodiments described above may be implemented by means of software, hardware, firmware or any combination thereof in various imaging systems, such as an X-ray digital fluoroscopic system. Such implementation is readily made by the ordinary skilled in the art, and will not be described in further details.

Figure 6:
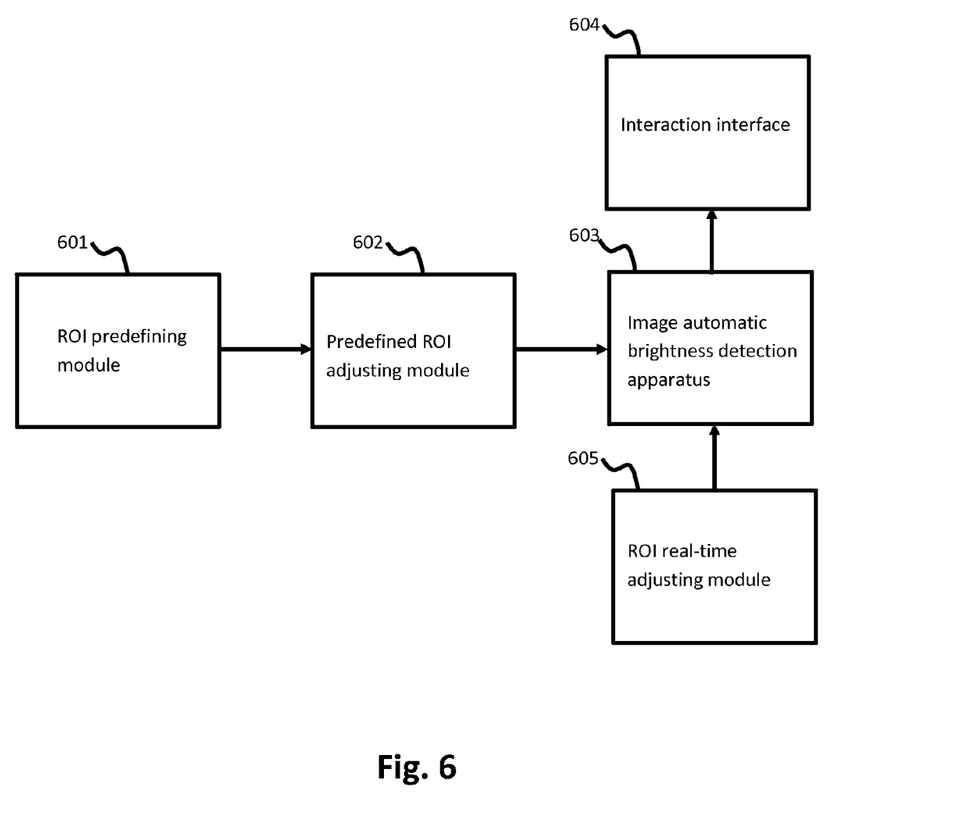
FIG. 6 is a schematic diagram of an apparatus for image automatic brightness detection according to an embodiment of the present invention.

FIG. 6 is a schematic diagram of an imaging system according to an embodiment. The imaging system comprises a ROI predefining module 601, a predefined ROI adjusting module 602, an image automatic brightness detection apparatus 603, a ROI display selecting module 604, and a ROI real-time adjusting module 605, wherein the ROI predefining module 601 is connected to the predefined ROI adjusting module 602 to input the predefined ROI to the predefined ROI adjusting module 602. The predefined ROI adjusting module 602 is connected to the image automatic brightness detection apparatus 603, which uses the predefined or adjusted predefined ROI as the initial position. The image automatic brightness detection apparatus 603 is also connected with the ROI display selecting module 604 for inputting the current ROI into the ROI display selecting module 604 for display. The image automatic brightness detection apparatus 603 is also connected with the ROI real-time adjusting module 605 for setting its ROI based on the adjusted ROI from the ROI real-time adjusting module 605.

When the imaging system is operating, the ROI predefining module 601 may be turned on or off, for making the determination whether or not the predefined ROI is inputted by a user. The user may define one or more ROIs based on the clinic application, the user's habit, patient's body form, etc.

When the imaging system is operating, the predefined ROI adjusting module 602 may be turned on or off, for making the determination whether or not it is necessary to adjust the predefined ROI. A user may review and adjust the predefined ROI at the outset of the fluoroscopic examination.

The image automatic brightness detection apparatus 603 uses the predefined ROI as the initial position, and the first frame selects the optimum ROI position in adjacent region of the predefined ROI, and every subsequent frame searches the optimum ROI position in adjacent region of the ROI selected for the previous frame and updates it.

When the imaging system is operating, the ROI display selecting module 604 may be turned on or off, for making the determination whether or not the ROI position is reviewed in real time. A user may turn on or off the ROI display during the fluoroscopic examination.

When the imaging system is operating, the ROI real-time adjusting module 605 may be turned on or off, for making the determination whether or not the ROI position is manually adjusted in real time. A user may review and manually adjust the ROI position in real time during the fluoroscopic examination. Starting from the adjusted next frame, the image automatic brightness detection method uses the adjusted ROI as the initial position, and every frame searches the optimum ROI position in adjacent region of the initial ROI and updates it.

Although the present invention has been described with reference to specific embodiments thereof, it is not intended that the present invention be limited to those specific embodiments. Those skilled in the art should be understood that various modifications, equivalent substitutions, changes, etc. may be made to the present invention. For example, one step or module in the above embodiment may be implemented by dividing it into two or more steps or modules, or on the contrary, two or more steps or modules in the above embodiment may be implemented by combining them into one step or module. However, these changes should fall within the scope of the present invention without departing from the spirit of the present invention. In addition, some terms as used in this specification and claims of this application are to be considered as illustrative and not restrictive. Furthermore, various references herein to "an embodiment", "an embodiment of the present invention", "one embodiment", "another embodiment", etc. refer to different embodiments of the present invention, and of course all or some of said embodiments may be incorporated into one embodiment or combinations thereof.

This written description uses examples to disclose the invention, including the best mode, and to also enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method for image automatic brightness detection, the method comprising:
   determining region of interest ROI candidates in an image;
   extracting features from each of the ROI candidates;
   selecting an optimum ROI candidate based on a weighted score of each of the ROI candidates by at least: queuing all the ROI candidates in descending order for each of the features, and determining a serial number of each of the ROI candidates in the queue as a score of the feature of the ROI candidate; and calculating the weighted score of each of the ROI candidates by multiplying the scores of the extracted features for each of the ROI candidates respectively by a predetermined weighting coefficient of the feature to obtain respective products and summing the products, wherein the ROI candidate with the smallest weighted score is selected as the optimum ROI; and
   calculating brightness value of the selected optimum ROI candidate as brightness feedback.

2. The method according to claim 1, wherein the determining ROI candidates in an image comprises calculating sizes of each of the ROI candidates and an extent of their overlapping in each direction.

3. The method according to claim 1, wherein the extracting features from each of the ROI candidates comprises at least one of:
   extracting features that are based on statistic characteristics of a grey-scale value for a pixel;
   extracting features that are based on relation between pixels; and
   extracting features that are based on image transformation.

4. The method according to claim 1, wherein the extracted features comprise:
   negative mean of pixels with maximum;
   negative mean of pixels with minimum; and
   edge information extracted by applying edge detection filter.

5. The method according to claim 4, wherein the pixels with the maximum refer to upper pixels from a predefined percentage of all pixel values ranked in descending order, and the pixels with the minimum refer to upper pixels from a predefined percentage of all pixel values ranked in ascending order.

6. The method according to claim 1, wherein the predetermined weighting coefficient is obtained for each of the extracted features by training.

7. The method according to claim 1, wherein calculating the brightness value of the selected optimum ROI candidate comprises:
   calculating mean values or median values of pixels, wherein pixels used to calculate the brightness value include all pixels, the pre-selected sampled pixels in the ROI, or a predetermined percentage of pixel intensity.

8. An apparatus for image automatic brightness detection, comprising:
   a determining module for determining region of interest (ROI) candidates in an image;
   an extracting module for extracting features from each of the ROI candidates;
   a selecting module for selecting an optimum ROI candidate based on a weighted score of each of the ROI candidates, wherein the selecting module further comprises: a queuing module for queuing all of the ROI candidates in descending order for each of the features, and determining serial number of each of the ROI candidates in the queue as score of the feature of the ROI candidate; and a calculating module for calculating the weighted score of each of the ROI candidates by multiplying the scores of the extracted features for each of the ROI candidates respectively by a predetermined weighting coefficient of the feature to obtain respective products and summing the products, wherein the ROI candidate with the smallest weighted score is selected as the optimum ROI; and
   a feedback module for calculating brightness value of the selected optimum ROI candidate as brightness feedback.

9. The apparatus according to claim 8, wherein the determination of the ROI candidates by the determining module comprises calculating sizes of the ROI candidates and their overlapping in each direction.

10. The apparatus according to claim 8, wherein the extracting module extracts at least one of:
    the features that are based on statistic characteristics of a grey-scale value for a pixel;
    the features that are based on relation between pixels; and
    the features that are based on image transformation.

11. The apparatus according to claim 8, wherein the extracting module extracts:
    negative mean of pixels with maximum;
    negative mean of pixels with minimum; and
    edge information extracted by applying edge detection filter.

12. The apparatus according to claim 11, wherein the pixels with the maximum refer to upper pixels from a predefined percentage of all pixel values ranked in descending order, and the pixels with the minimum refer to upper pixels from a predefined percentage of all pixel values ranked in ascending order.

13. The apparatus according to claim 8, wherein the predetermined weighting coefficient is obtained for each of the extracted features by training.

14. The apparatus according to claim 8, wherein the calculation of the brightness value of the selected optimum ROI candidate by the feedback module comprises:
    calculating mean values or median values of pixels, wherein pixels used to calculate the brightness value include all pixels, the pre-selected sampled pixels in the ROI, or a predetermined percentage of pixel intensity.

* * * * *